US012631613B2

(12) United States Patent
Wu et al.

(10) Patent No.: US 12,631,613 B2
(45) Date of Patent: May 19, 2026

(54) IN SITU U-Pb DATING METHOD FOR CALCITE

(71) Applicant: Institute of Geology and Geophysics, Chinese Academy of Sciences, Beijing (CN)

(72) Inventors: Shitou Wu, Beijing (CN); Yueheng Yang, Beijing (CN); Hao Wang, Beijing (CN); Lei Xu, Beijing (CN); Chao Huang, Beijing (CN); Liewen Xie, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 862 days.

(21) Appl. No.: 18/053,840

(22) Filed: Nov. 9, 2022

(65) Prior Publication Data

US 2024/0151704 A1     May 9, 2024

(51) Int. Cl.
*G01N 33/24* (2006.01)
*G01N 1/28* (2006.01)
(Continued)

(52) U.S. Cl.
CPC ............. *G01N 33/24* (2013.01); *G01N 1/286* (2013.01); *G01N 30/7253* (2013.01);
(Continued)

(58) Field of Classification Search
CPC .. G01N 1/286; G01N 30/7253; G01N 33/202; G01N 33/24; G01N 2001/2873; G01N 2001/364
(Continued)

(56) References Cited

U.S. PATENT DOCUMENTS 8,901,485 B1 * 12/2014 Donelick ............ H01J 49/0009
250/284

FOREIGN PATENT DOCUMENTS

CN     106483189 A  *  3/2017  ............. G01N 27/64
CN     110376273 A  * 10/2019  ............. G01N 27/62
(Continued)

OTHER PUBLICATIONS

Chen, W. et al., Chemical Geology 2013, 353, 151-172. (Year: 2013).*
(Continued)

*Primary Examiner* — Arlen Soderquist
(74) *Attorney, Agent, or Firm* — McDonnell Boehnen Hulbert & Berghoff LLP

(57) ABSTRACT

The present disclosure discloses an in situ U—Pb dating method for calcite, including: cutting a calcite sample to prepare an epoxy resin sample target; placing the sample in a laser ablation sample chamber, and adjusting a position of the sample in an optical axis direction; conducting line scanning ablation on the sample target, and measuring ion signal intensity data of $^{43}Ca$, $^{88}Sr$, $^{139}La$, and $^{238}U$; conducting two-dimensional (2D) element imaging to obtain a 2D element content distribution map; according to the 2D element content distribution map, determining a high-U analysis target area, conducting point ablation on the high-U target area, and measuring ion signal intensity data of $^{206}Pb$, $^{207}Pb$, and $^{238}U$; and after the element signal data is obtained, calculating $^{207}Pb/^{206}Pb$ and $^{238}U/^{206}Pb$ fractionation coefficients, correcting ratios of an unknown sample, constructing a Tera-Wasserbug diagram, and calculating age data and an initial Pb isotope ($^{207}Pb/^{206}Pb$) composition of the calcite sample.

1 Claim, 18 Drawing Sheets

(51) Int. Cl.
|         |           |
|---------|-----------|
| *G01N 30/72*  | (2006.01) |
| *G01N 33/202* | (2019.01) |
| *G01N 1/36*   | (2006.01) |

(52) U.S. Cl.
CPC ... *G01N 33/202* (2019.01); *G01N 2001/2873*
(2013.01); *G01N 2001/364* (2013.01)

(58) Field of Classification Search
USPC ........................................................ 436/28
See application file for complete search history.

(56) References Cited

FOREIGN PATENT DOCUMENTS

| CN | 111007141 A | * | 4/2020 | ............. G01N 27/64 |
|----|-------------|---|--------|-------------------------|
| CN | 113624830 A | * | 11/2021 | ............. G01N 1/286 |

OTHER PUBLICATIONS

Roberts, N. M. W. et al., Geochronology, 2020, 2, 33-61. (Year: 2020).*
Rasbury, E. T. et al., Geochronology, 2021, 3, 103-122. (Year: 2021).*
Yang, F. et al., Minerals 2021, 11, article 450, 21 pages. (Year: 2021).*

* cited by examiner

IN SITU U-Pb DATING METHOD FOR CALCITE

TECHNICAL FIELD

The present disclosure relates to the technical field of geological exploration, and in particular, to an in situ U—Pb dating method for calcite.

BACKGROUND

Calcite (with a chemical formula of $CaCO_3$), as a common mineral, widely exists in various geological environments. Calcite can contain a certain amount of uranium (U) (<10 μg g$^{-1}$) and a small amount of lead (Pb) in the crystallization process, which has the potential for U—Pb dating. The calcite U—Pb dating technology has great application potential, especially in the aspects of paleoenvironment, sedimentary process, diagenesis, structural deformation, ore genesis, carbohydrate migration, etc. The previous age determination of these geological processes is mainly based on indirect minerals, such as biotite Ar—Ar dating. However, dating based on indirect minerals is often controversial, for example, indirect minerals cannot represent the age of geological processes. Calcite is the direct mineral of these geological processes, so the calcite U—Pb dating technology can provide important chronological data for these geological processes.

The traditional U—Pb dating of calcite mainly adopts isotope dilution-thermal ionization mass spectrometry (ID-TIMS). This technology obtains data through four steps: sample drilling, acid dissolution and digestion, separation and purification, and computer testing. ID-TIMS can provide high-precision data quality, but the technical operation process is complex, takes a long time (>2 weeks), and the amount of data obtained is limited. In addition, as a whole analysis technology, ID-TIMS has low spatial resolution, which makes it have great limitations in analysis of samples with belt changes. Laser ablation-inductively coupled plasma-mass spectrometry (LA-ICP-MS) is widely used in U—Pb geochronology. LA-ICP-MS has the advantages of cost-effectiveness, simple maintenance, and fast analysis (single point analysis<3 minutes). However, the calcite usually has a low U content (<10 μg g$^{-1}$), which requires increasing the sampling amount (laser ablation beam spot) to obtain a sufficiently high signal intensity. However, increasing the laser beam spot significantly reduces the spatial resolution, which is not conducive to calcite with complex composition changes. In addition, the U and Pb contents of calcite are extremely uneven at the micrometer scale, so how to accurately determine the sampling location is also a difficulty in this technology.

SUMMARY

In view of the shortcomings of the prior art, the present disclosure provides an in situ U—Pb dating method for calcite.

To achieve the objective of the present disclosure, the technical solutions of the present disclosure are as follows:

An in situ U—Pb dating method for calcite includes the following steps:

1) cutting a calcite sample or a rock sample containing calcite to prepare an epoxy resin sample target with a diameter of 1 inch and a thickness of about 5 mm to adapt to a size of a laser ablation sample chamber;

2) placing the sample in the laser ablation sample chamber, and adjusting a position of the sample in an optical axis direction to make a laser beam focus well;

3) conducting line scanning ablation on calcite in the sample target using the laser beam, loading ablated aerosol into a quadrupole inductively coupled plasma mass spectrometry (ICP-MS) plasma source for ionization using a helium gas as a carrier gas, and measuring ion signal intensity data of $^{43}Ca$, $^{88}Sr$, $^{139}La$, and $^{238}U$;

4) conducting two-dimensional (2D) element imaging using Iolite 4 software to obtain a 2D element content distribution map;

5) according to the 2D element content distribution map, determining a high-U analysis target area, conducting point ablation on the high-U target area using the laser beam, loading ablated aerosol into a double-focusing sector field ICP-MS plasma source for ionization using a carrier gas, and measuring ion signal intensity data of $^{206}Pb$, $^{207}Pb$, and $^{238}U$;

6) in a measurement process, after every ten unknown samples are tested, repeatedly testing two calibration reference materials NIST SRM 614 (for $^{207}Pb/^{206}Pb$ correction), three calibration reference materials WC-1 (for $^{238}U/^{206}Pb$ correction), and two quality monitoring reference materials Duff Brown Tank to ensure same measurement conditions for the reference materials and the unknown samples;

7) after the element signal data is obtained, obtaining corresponding fractionation coefficients according to measured values and standard values of $^{207}Pb/^{206}Pb$ and $^{238}U/^{206}Pb$ of the reference materials, and correcting $^{207}Pb/^{206}Pb$ and $^{238}U/^{206}Pb$ ratios of the unknown sample; and 8) constructing a Tera-Wasserbug diagram through the corrected $^{207}Pb/^{206}Pb$ and $^{238}U/^{206}Pb$ ratios, and calculating age data and an initial Pb isotope ($^{207}Pb/^{206}Pb$) composition of the calcite sample.

Compared with the prior art, the present disclosure has the following advantages:

The method integrates the existing LA-ICP-MS U—Pb dating measurement mode, and uses a highly sensitive interface cone and auxiliary nitrogen to sensitize the instrument. In addition, a two-step measurement process is adopted, namely (1) 2D element imaging, and (2) selection of a target area with a high U content for U—Pb dating. The method overcomes the shortcomings of the prior art, such as long test period, less sample analysis, low spatial resolution, and low success rate.

BRIEF DESCRIPTION OF THE DRAWINGS

FIG. 5A shows S+H cone group+Ar plasma, FIG. 5B shows Jet+H cone group+Ar plasma, and FIG. 5C shows Jet+X cone group+Ar-N$_2$ plasma.

FIG. 8A shows results of JT calcite, FIG. 8B shows results of JT calcite surrounding rock, U contents of two tests are also listed accordingly, and a 110-micron laser beam spot is used.

DETAILED DESCRIPTION OF THE EMBODIMENTS

Figure 1:
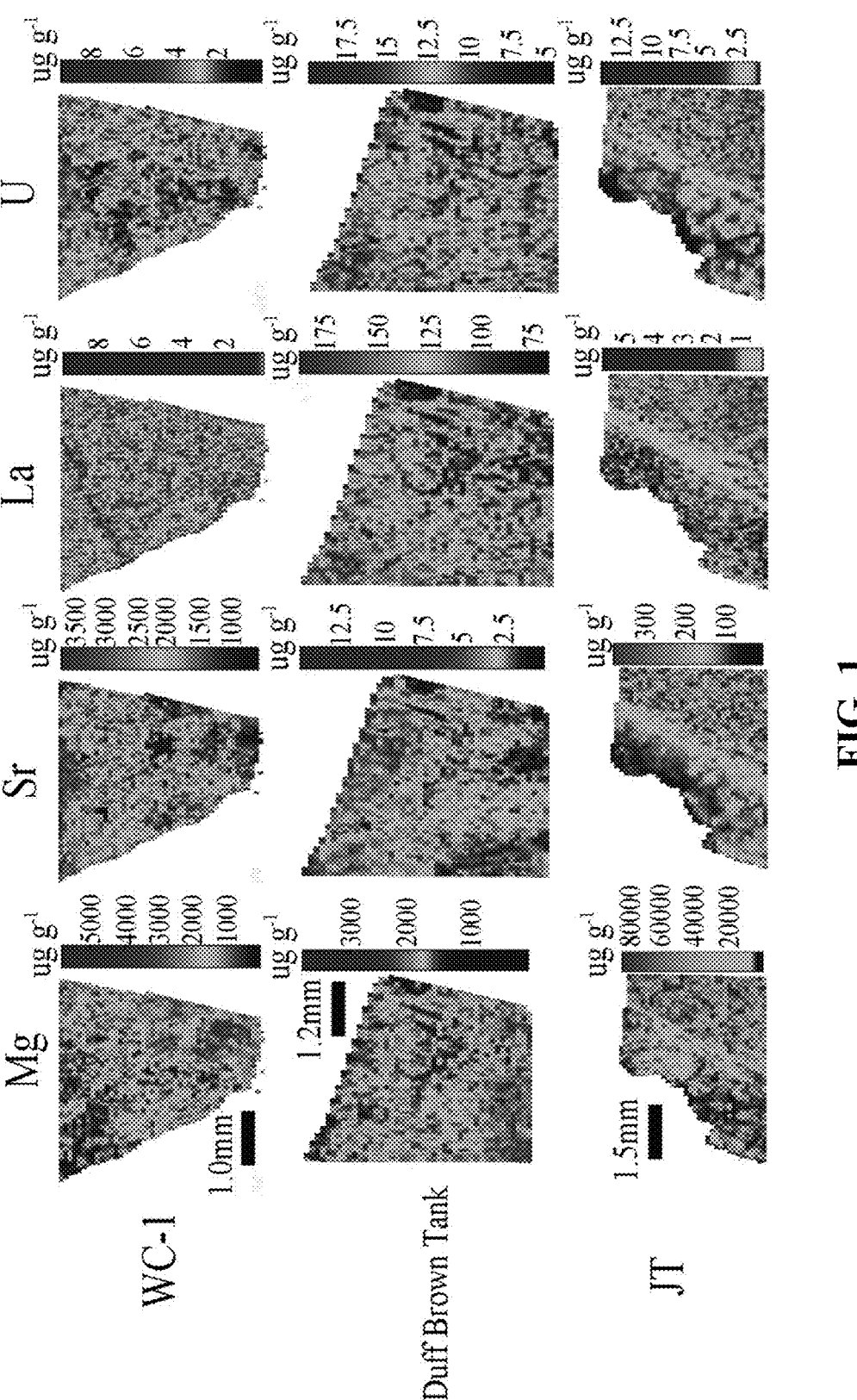
FIG. 1 is a 2D element content distribution map in an example of the present disclosure.

To make the objectives, technical solutions, and advantages of the present disclosure clearer, the following further describes the present disclosure in detail according to the accompanying drawings and examples.

An in situ uranium-lead dating method for calcite included the following steps.

1) The specific implementation of the technical method of the present disclosure was introduced with four calcite age reference materials: WC-1 (254±6.4 Ma), Duff Brown Tank (64.04±0.67 Ma), JT (13.797±0.031 Ma), and ASH-15 (2.965±0.011 Ma). The U contents of the four calcite standard samples were widely distributed (0.5-20 μg g$^{-1}$), which fully demonstrated the universality of this method for various calcites. These known ages were used as validation criteria in the method to verify the accuracy and precision of the method.

2) First, the above calcite samples were cast into sample targets (with a diameter of 1 inch and a thickness of about 5 mm) with epoxy resin, which were lightly polished to expose the calcite sections, and polished, cleaned, and dried for standby.

3) The calcite sample targets were placed into a laser ablation instrument chamber, and the sample chamber was purged with a helium gas to fill it with the helium gas.

4) An NIST SRM 612 glass reference material was used to optimize the conditions of the quadrupole ICP-MS instrument, making $^{206}$Pb and $^{238}$U signals optimal, while ensuring that the oxide yield (ThO$^+$/Th$^+$) was less than 1.0%, the secondary ion yield (Ca$^{2+}$/Ca$^+$) was less than 2.0%, and the Th$^+$/U$^+$ signal ratio was between 0.95 and 1.05.

5) In the line scanning mode, the laser beam spot was adjusted to be circular, with a diameter of 50 μm, a laser energy density of 2.0 J/cm$^2$, an ablation frequency of 15 Hz, and a line scanning speed of 40 μm/s, and area scanning was conducted. The area scanning area was generally 5.0 mm*5.0 mm.

6) The acquisition procedure was: 10 seconds of blank before instrument analysis, several seconds of laser ablation line scanning of data (depending on the length of the line), and 10 seconds of blank after instrument analysis. After each line scanning of 10 unknown samples, one NIST SRM 612 glass reference material was repeatedly tested (for instrument drift correction and element content calculation) to ensure same measurement conditions for the reference materials and the unknown samples.

7) In this example, during 2D element imaging, the ions to be measured and the mass numbers to be characterized were $^{24}$Mg, $^{29}$Si, $^{43}$Ca, $^{55}$Mn, $^{57}$Fe, $^{69}$Ga, $^{85}$Rb, $^{88}$Sr, $^{90}$Zr, $^{137}$Ba, $^{139}$La, $^{140}$Ce, $^{141}$Pr, $^{146}$Nd, $^{147}$Sm, $^{153}$Eu, $^{158}$Gd, $^{159}$Tb, $^{163}$Dy, $^{165}$Ho, $^{166}$Er, $^{169}$Tm, $^{173}$Yb, $^{175}$Lu, $^{206}$Pb, $^{207}$Pb, $^{208}$Pb, $^{232}$Th, and $^{238}$U, and the measurement integration time was 6 milliseconds.

8) The Iolite software (version 4.0) was used to process the data offline. First, the instrument blank deduction was conducted for the signal, and the instrument drift correction was conducted to calculate signal intensities of different elements. According to the signal intensity and content of each element of NIST SRM 612, an instrument response coefficient is calculated, as shown in the following formula (1).

$$k_{el} = \frac{I_{el}^{Standard\ sample\ 612}}{C_{el}^{Standard\ sample\ 612}}, \tag{1}$$

where k is the instrument response coefficient, el is an element, I is the signal intensity, and C is the element content.

A content of an unknown sample is calculated by formula (2) according to the instrument response coefficient, and a 2D element content distribution map is imaged.

$$C_{el}^{Unknown\ sample} = \frac{I_{el}^{Unknown\ sample}}{k_{el}} \tag{2}$$

2D element content map, as shown in FIG. 1.

9) According to the 2D element content distribution map, a high-U analysis target area was determined, point ablation was conducted on the high-U target area using the laser beam (a laser beam spot diameter of 50-110 μm, a laser energy density of 2.0 J/cm$^2$, and an ablation frequency of 10 Hz), ablated aerosol was loaded into a double-focusing sector field ICP-MS plasma source for ionization using a carrier gas, and ion signal intensity data of $^{206}$Pb, $^{207}$Pb, and $^{238}$U were measured.

10) The acquisition procedure was: 5 seconds of blank before instrument analysis, 30 seconds of laser ablation line scanning of data, and 10 seconds of blank after instrument analysis. After each operation on 10 unknown samples, two NIST SRM 614 were repeatedly tested (for $^{207}$Pb/$^{206}$Pb correction), three WC-1 were repeatedly tested (for $^{238}$U/$^{206}$Pb correction), and two Duff Brow Tank were repeatedly tested (for data quality monitoring), so as to ensure same measurement conditions for the reference materials and the unknown samples.

11) In the present disclosure, during U—Pb dating experiment, the ions to be measured and the mass numbers to be characterized were $^{202}$Hg, $^{204}$Pb, $^{206}$Pb, $^{207}$Pb, $^{208}$Pb, $^{232}$Th, $^{235}$U, and $^{238}$U, and the measurement integration times were 2 milliseconds, 2 milliseconds, 15 milliseconds, 25 milliseconds, 2 milliseconds, 2 milliseconds, 2 milliseconds, and 10 milliseconds.

12) The Iolite software (version 3.7) was used to process the data offline. First, the instrument blank deduction was conducted for the signal, and the instrument drift correction was conducted. The $^{207}Pb/^{206}Pb$ and $^{238}U/^{206}Pb$ ratios were calculated. The element fractionation curve was simulated according to NIST SRM 614 and used to correct the element fractionation of unknown samples. According to NIST SRM 614 and WC-1, instrument fractionation coefficients of $^{207}Pb/^{206}Pb$ and $^{238}U/^{206}Pb$ are calculated, as shown in the following formulas (3) and (4).

$$k_{7/6} = \frac{\dfrac{207_{Pb} \text{ Standard sample } 614}{206_{Pb} \text{ Measured value}}}{\dfrac{207_{Pb} \text{ Standard sample } 614}{206_{Pb} \text{ Recommended value}}}, \qquad (3)$$

where k is the instrument fractionation coefficient, and 7/6 is the abbreviation for the $^{207}Pb/^{206}Pb$ ratio.

$$k_{8/6} = \frac{\dfrac{238_{U} \text{ Standard sample } WC-1}{206_{Pb} \text{ Measured value}}}{\dfrac{238_{U} \text{ Standard sample } WC-1}{206_{Pb} \text{ Recommended value}}}, \qquad (4)$$

where 8/6 is the abbreviation for the $^{238}U/^{206}Pb$ ratio.

The $^{207}Pb/^{206}Pb$ and $^{238}U/^{206}Pb$ ratios of unknown samples are corrected according to the fractionation coefficient, as shown in the following formulas:

$$\frac{207_{Pb} \text{ Unknown sample}}{206_{Pb} \text{ Corrected value}} = \frac{\dfrac{207_{Pb} \text{ Unknown sample}}{206_{Pb} \text{ Measured value}}}{k_{7/6}}, \text{ and} \qquad (5)$$

$$\frac{238_{U} \text{ Unknown sample}}{206_{Pb} \text{ Corrected value}} = \frac{\dfrac{238_{U} \text{ Unknown sample}}{206_{Pb} \text{ Measured value}}}{k_{8/6}}. \qquad (6)$$

Figure 2:
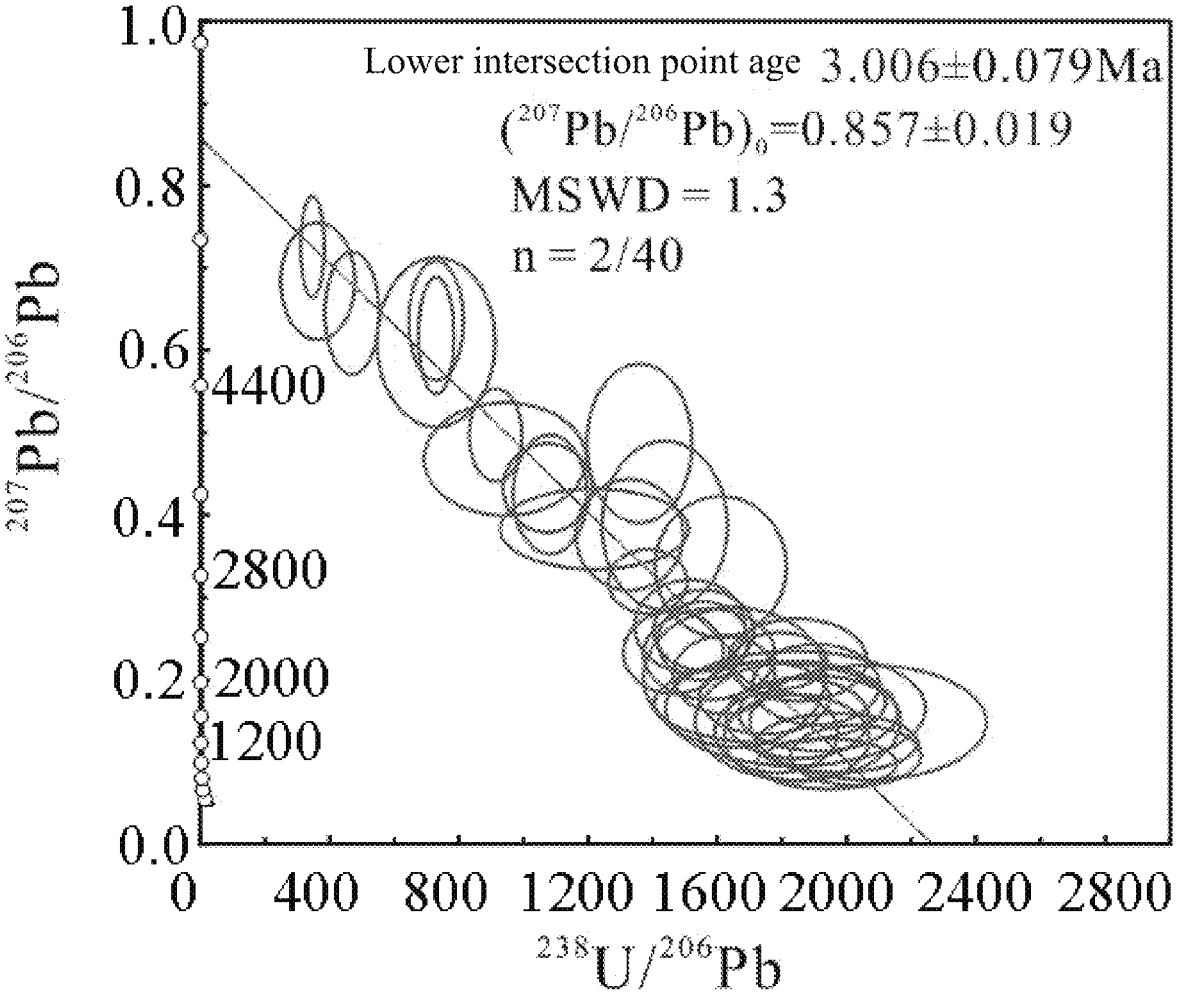
FIG. 2 is an age data and initial Pb isotope ($^{207}Pb/^{206}Pb$) composition diagram of a calcite sample in the example of the present disclosure.

A Tera-Wasserbug diagram is constructed according to the corrected $^{207}Pb/^{206}Pb$ and $^{238}U/^{206}Pb$ ratios, and age data and an initial Pb isotope ($^{207}Pb/^{206}Pb$) composition of the calcite sample are calculated, as shown in FIG. 2.

Figure 3:
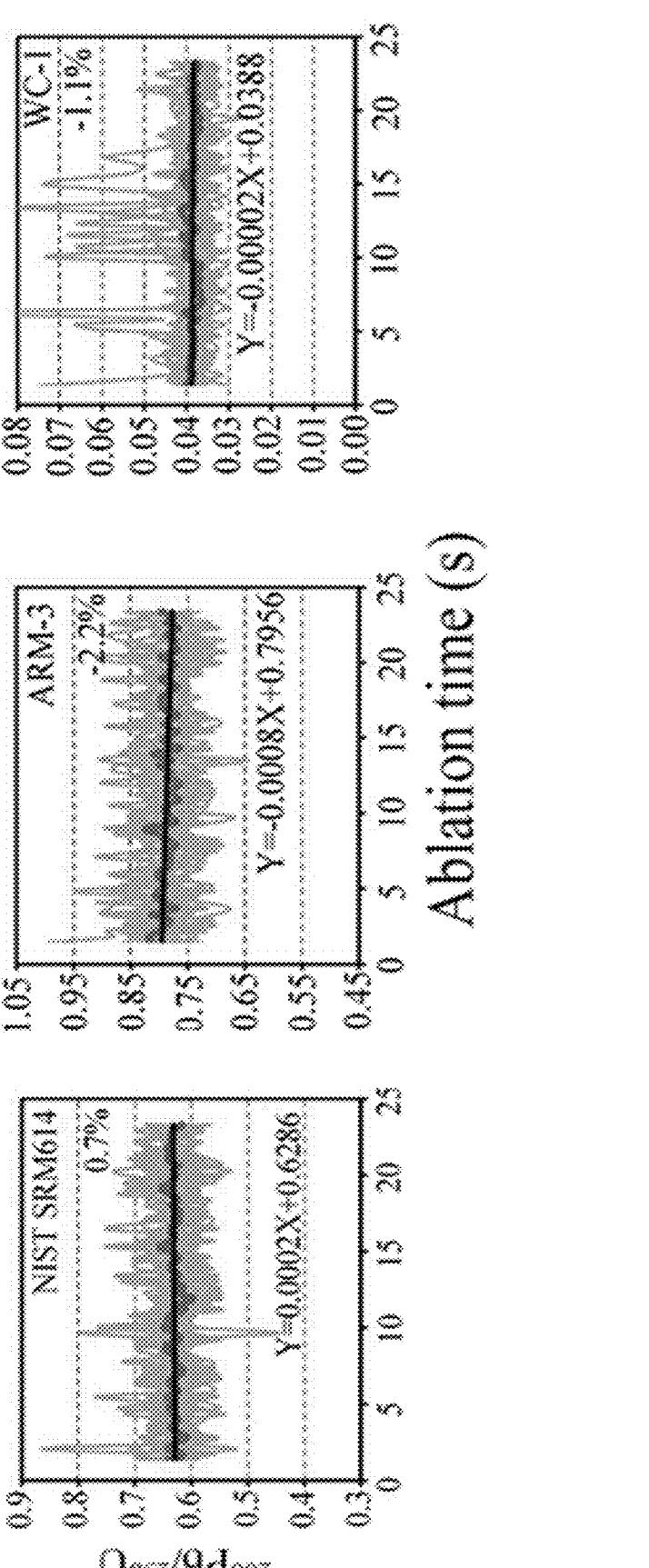
FIG. 3 shows element fractionation effect result diagrams of NIST SRM 614, ARM-3, and WC-1 in the example of the present disclosure.

The element fractionation effect of LA-ICP-MS was one of the main reasons that affected the accuracy and precision of data results. Therefore, the present disclosure took NIST SRM 614, ARM-3, and WC-1 as examples to explore the element fractionation effect. The results are shown in FIG. 3. It can be seen from the figure that the fractionation effects of the three different matrix elements are similar, so the fractionation model of NIST STM 614 can be directly used for the element fractionation correction of calcite.

Figure 4:
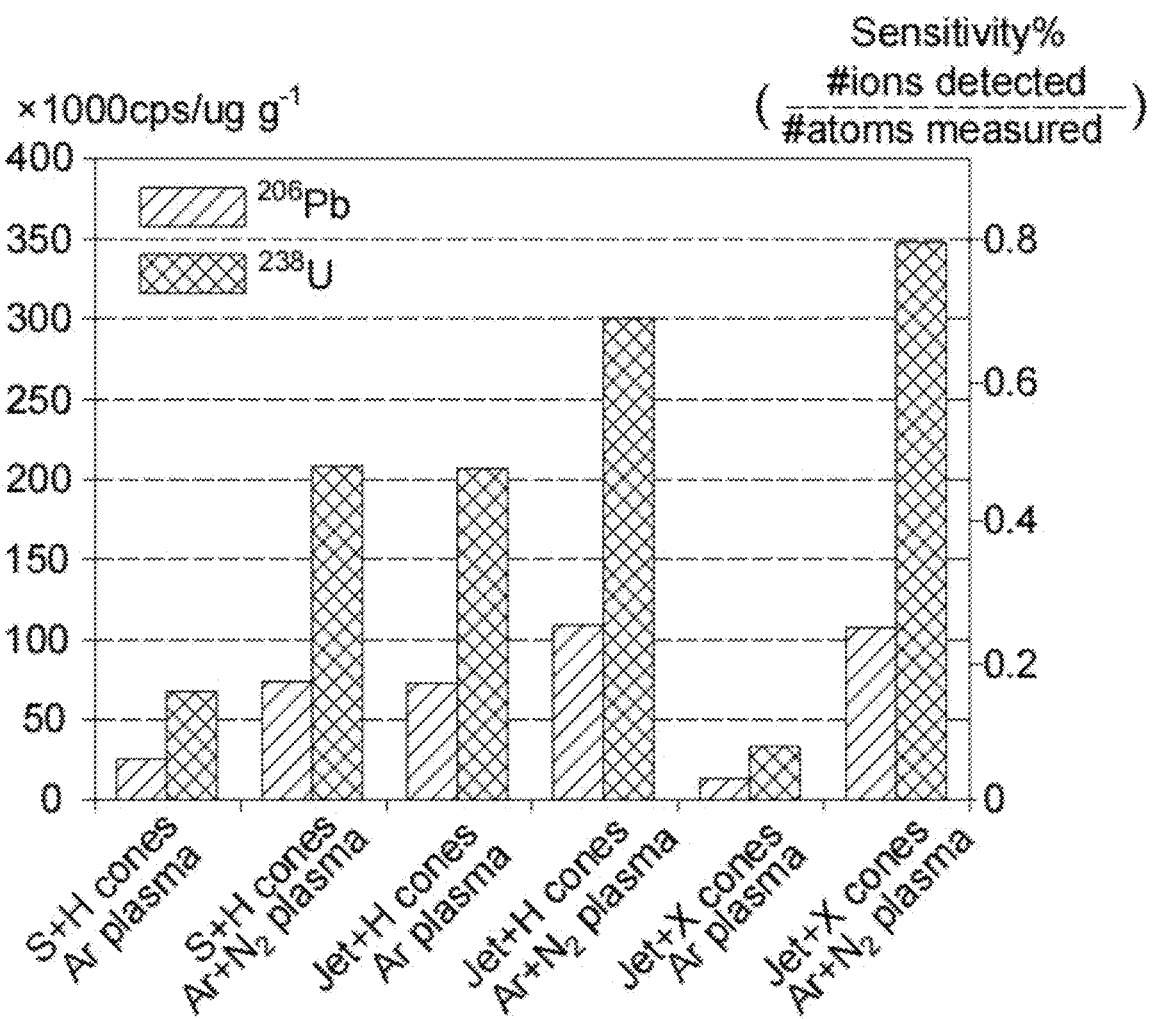
FIG. 4 is a sensitization effect diagram of auxiliary nitrogen addition in different cone groups on the instrument in the example of the present disclosure.

The low U content of calcite required high instrument sensitivity. Therefore, the present disclosure explored the sensitization effect of auxiliary nitrogen addition in different cone groups on the instrument. Under six modes (S+H cone group+Ar plasma, S+H cone group+AR-N₂ plasma, Jet+H cone group+Ar plasma, Jet+H cone group+AR-N₂ plasma, Jet+X cone group+Ar plasma, and Jet+X cone group+AR-N₂ plasma), instrument parameters were adjusted, making $^{206}Pb$ and $^{238}U$ signals optimal, while ensuring that the oxide yield (ThO⁺/Th⁺) was less than 1.0%, the secondary ion yield (Ca²⁺/Ca⁺) was less than 2.0%, and the Th⁺/U⁺ signal ratio was between 0.95 and 1.05. The results are shown in FIG. 4. It can be seen from the figure that the signal intensity is optimal under the condition of Jet+X cone group+Ar-N₂ plasma instrument, and the instrument sensitivity is increased by 3-5 times.

Figure 5A:
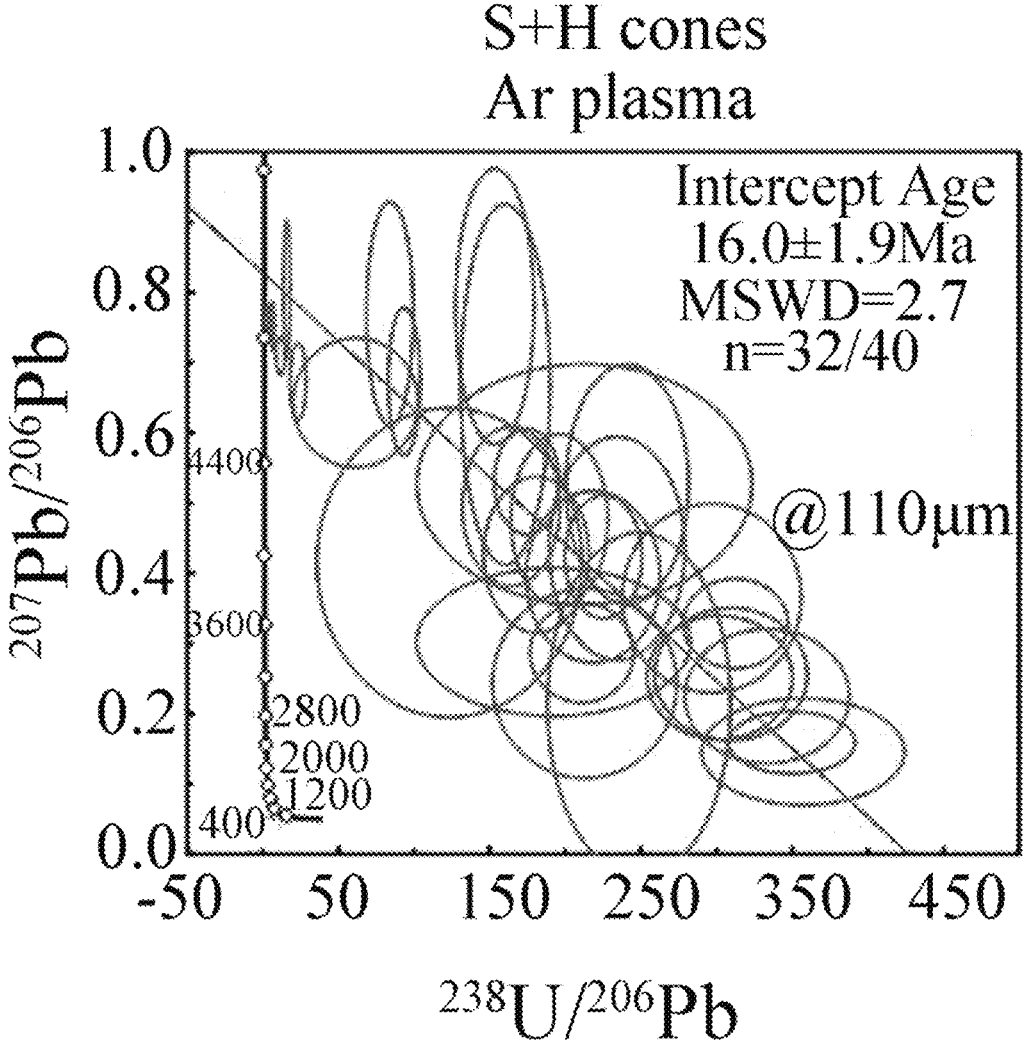
FIG. 5A-C show analysis result diagrams of JT in the example of the present disclosure, where
Figure 5B:
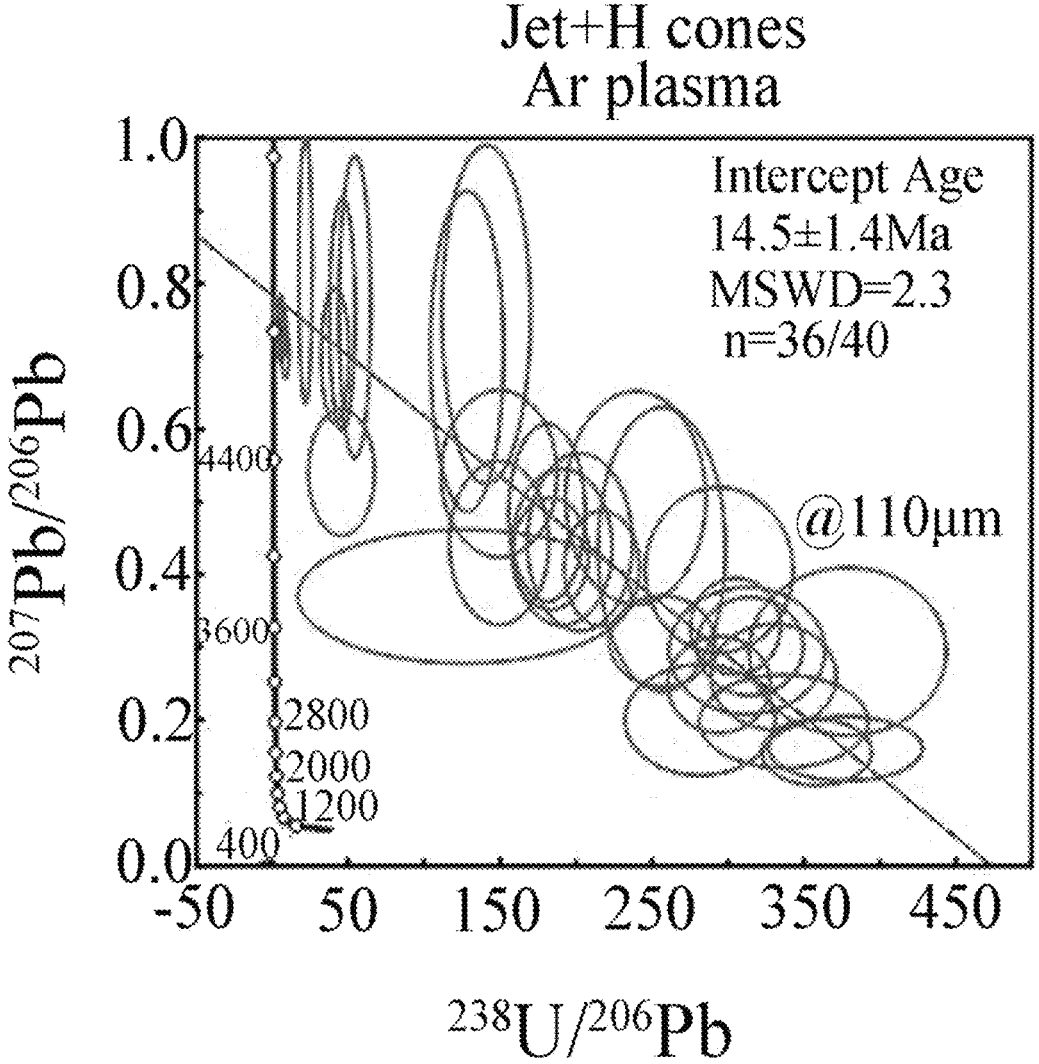
Figure 5C:
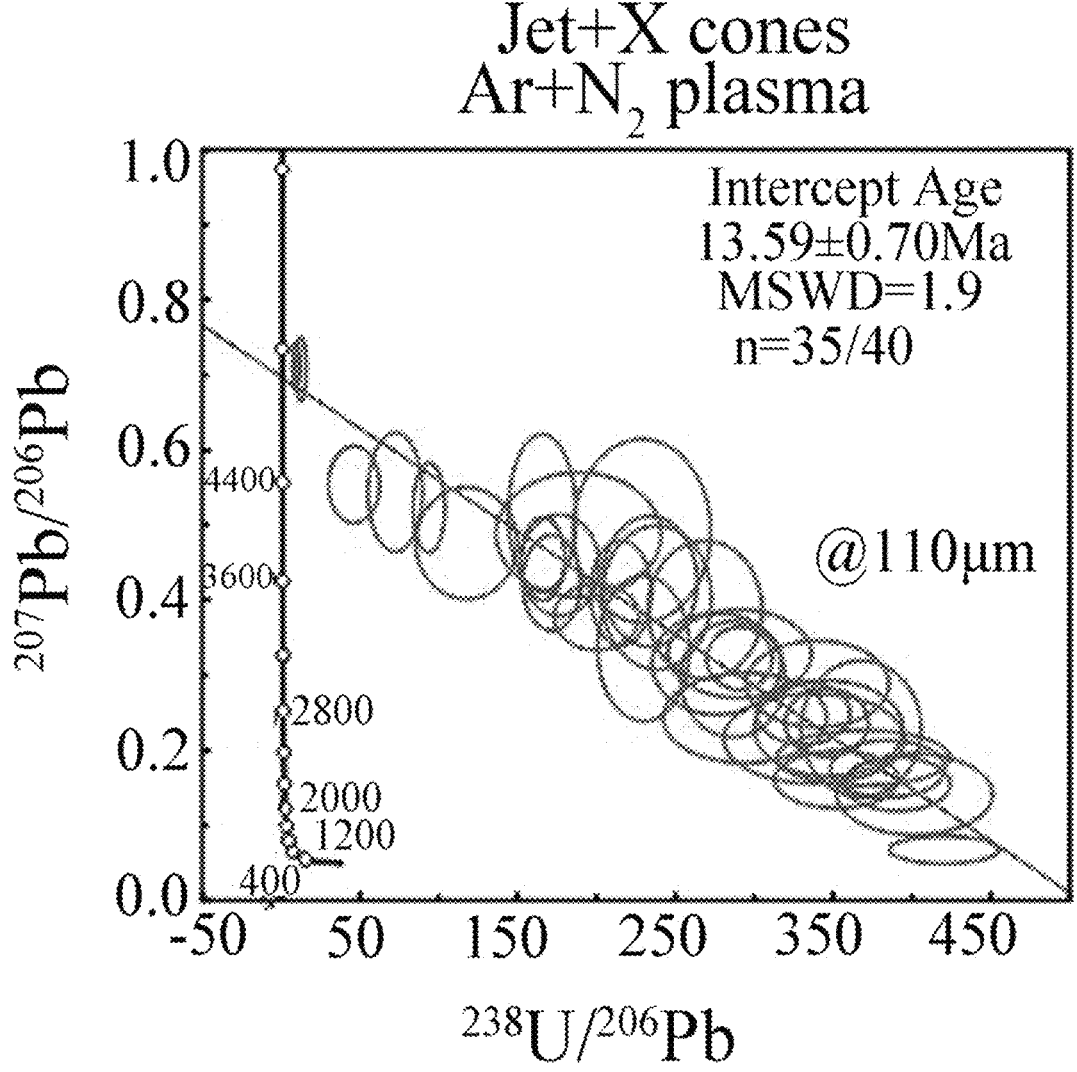
Figure 6A:
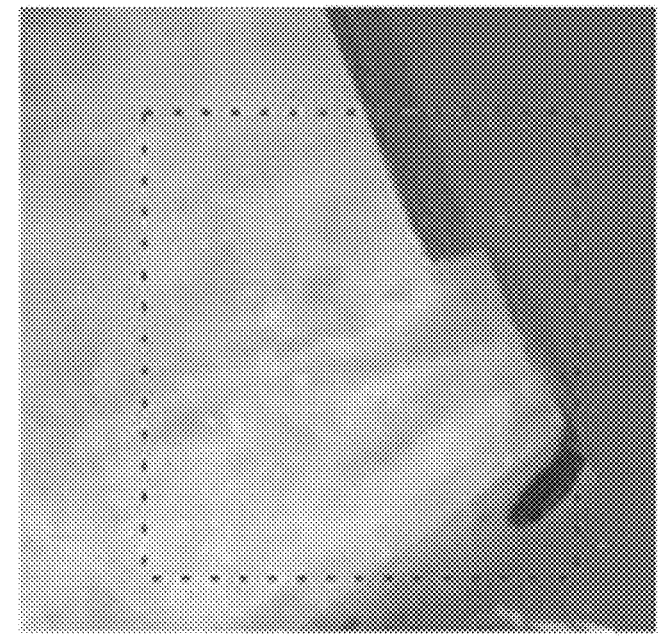
FIG. 6A-C show comparison diagrams of results of a two-step method (FIG. 6B) and a one-step method (FIG. 6C) in the example of the present disclosure.
Figure 6A:
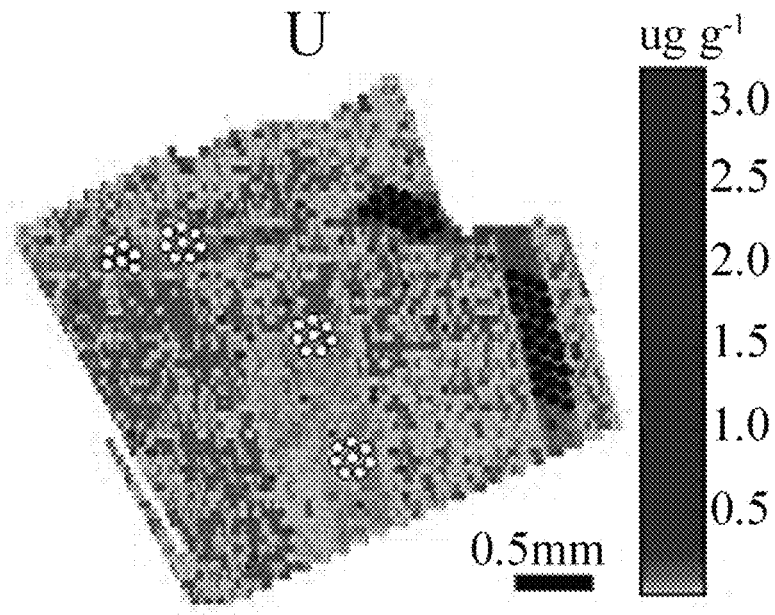
Figure 6B:
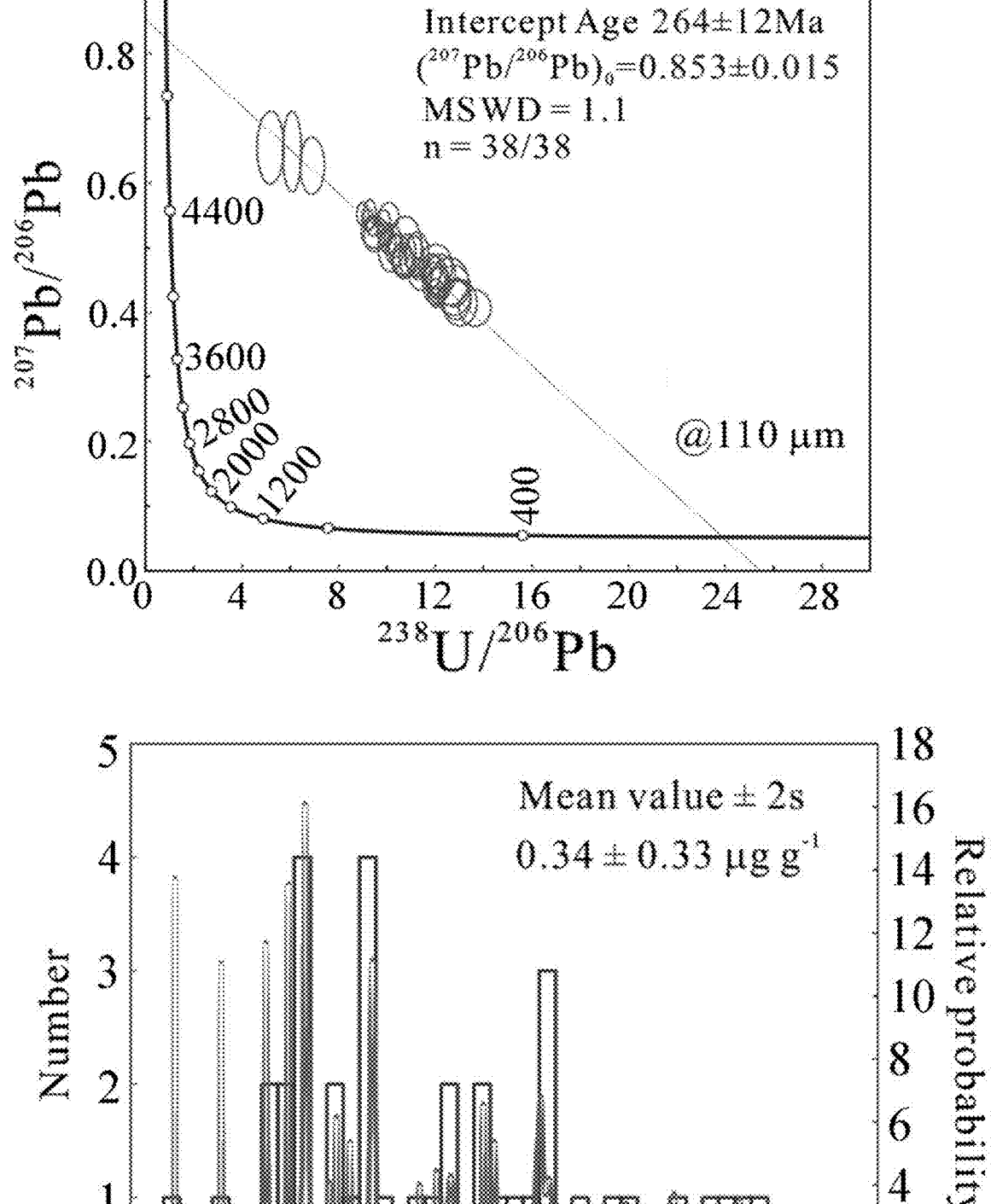
Figure 6C:
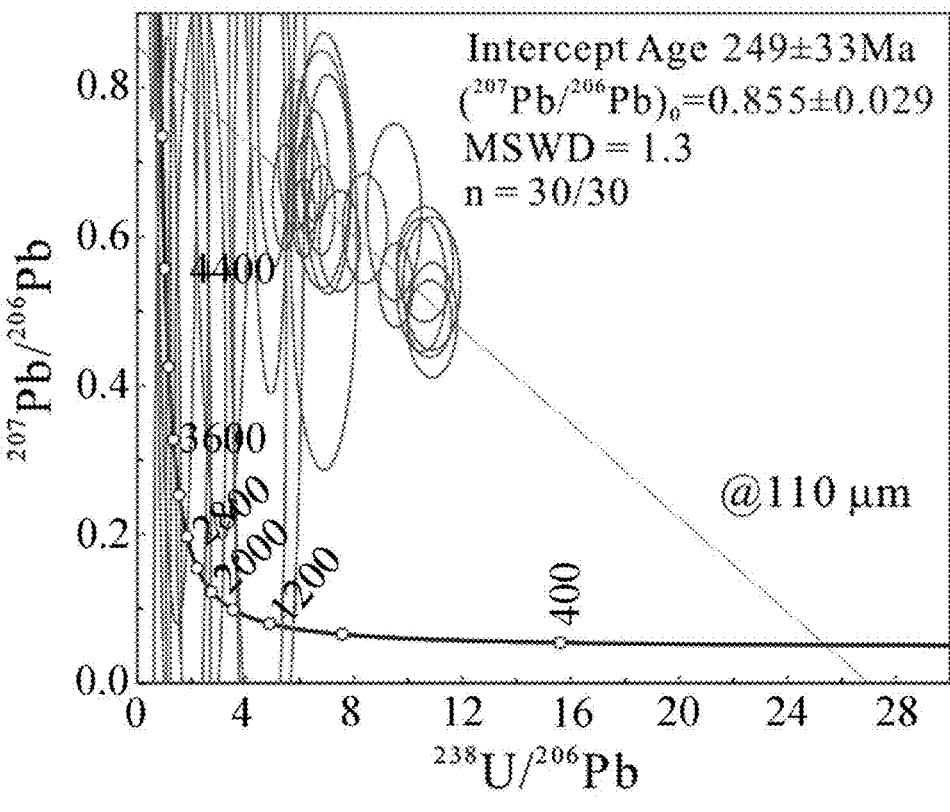
Figure 6C:
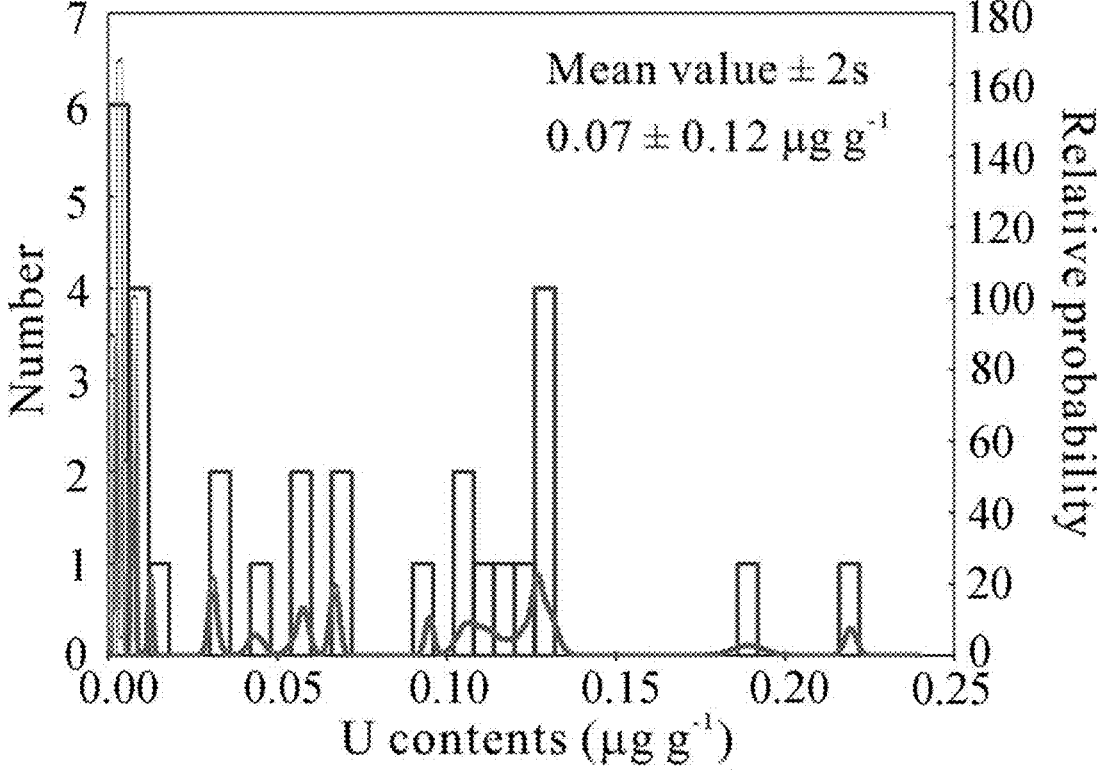
Figure 7A:
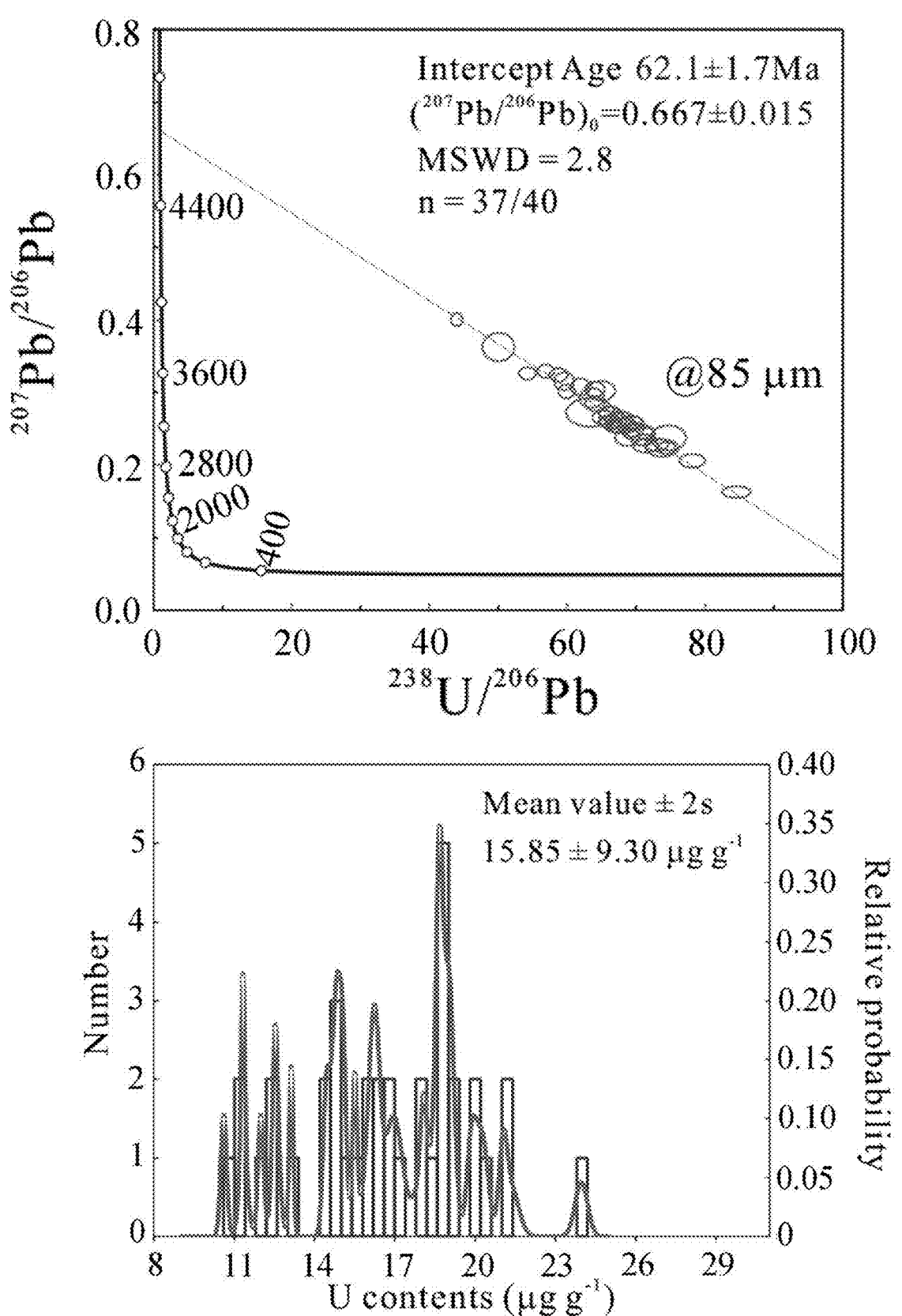
FIG. 7A-D show analysis result diagrams of Duff Brown Tank in the example of the present disclosure, where FIGS. 7A, 7B, 7C, and 7D respectively represent results of four independent tests at different times, U contents of the four tests are also listed correspondingly, FIGS. 7A, 7B, and 7C use an 85-micron laser beam spot, and FIG. 7D uses a 50-micron laser beam spot.
Figure 7B:
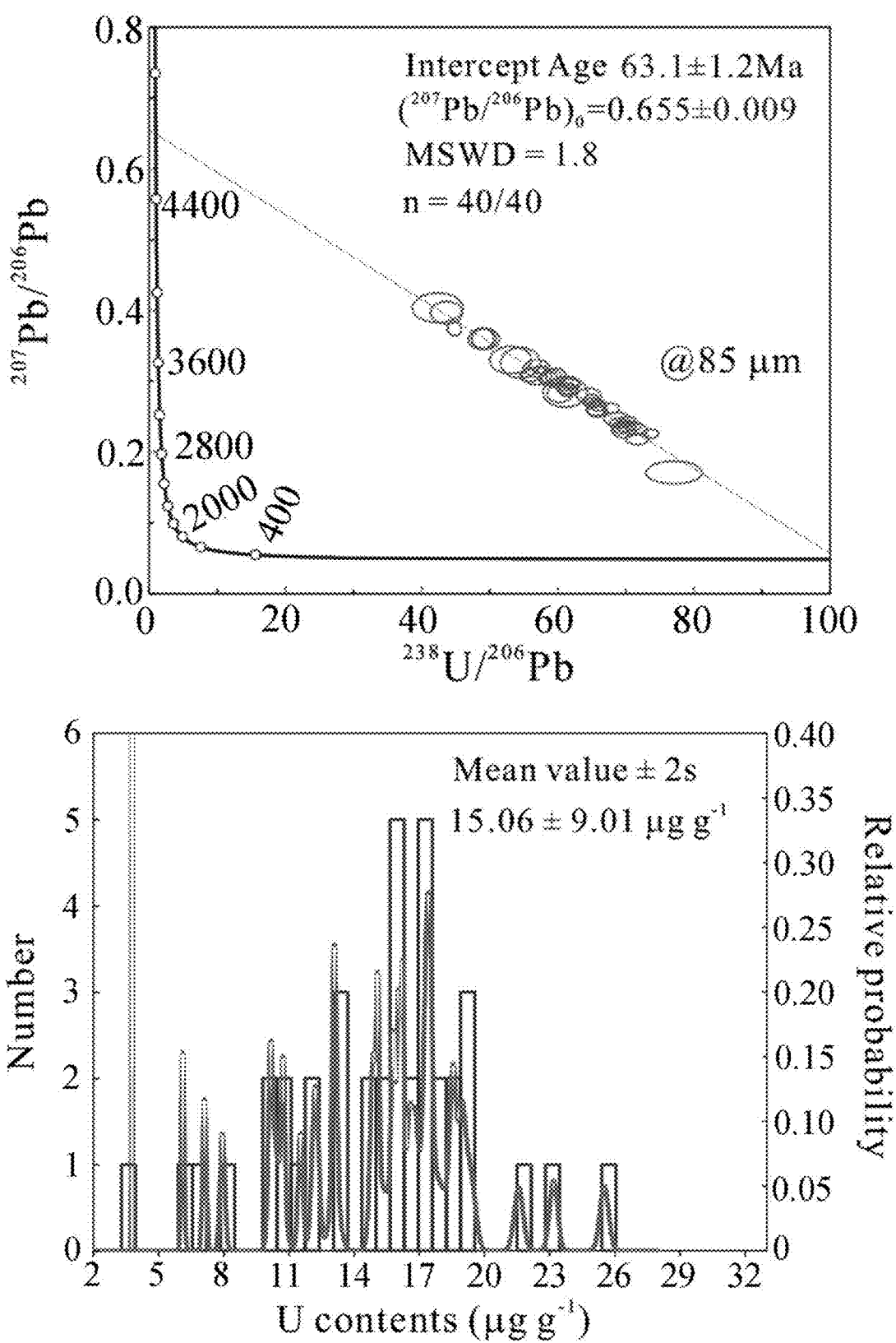
Figure 7C:
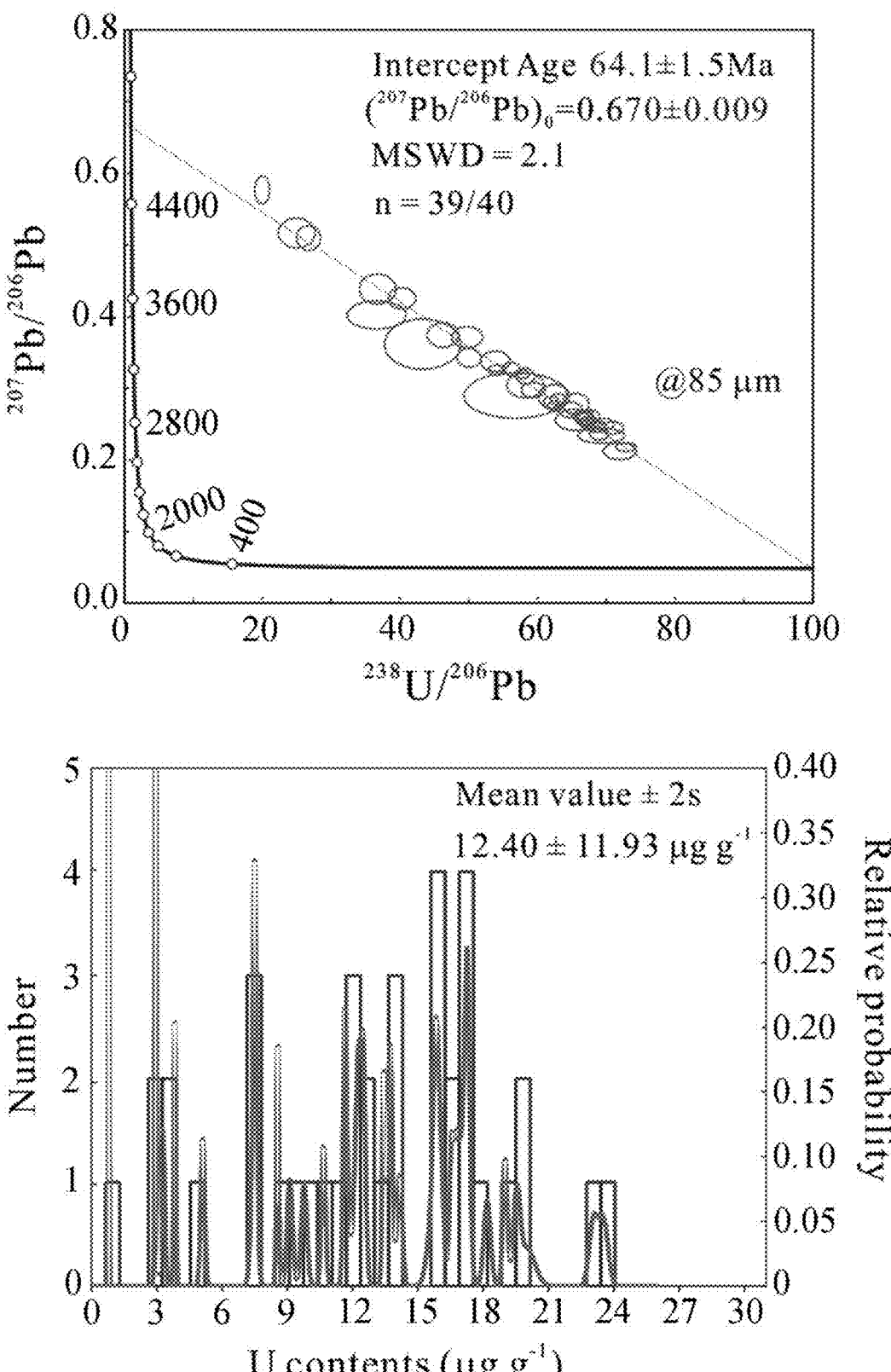
Figure 7D:
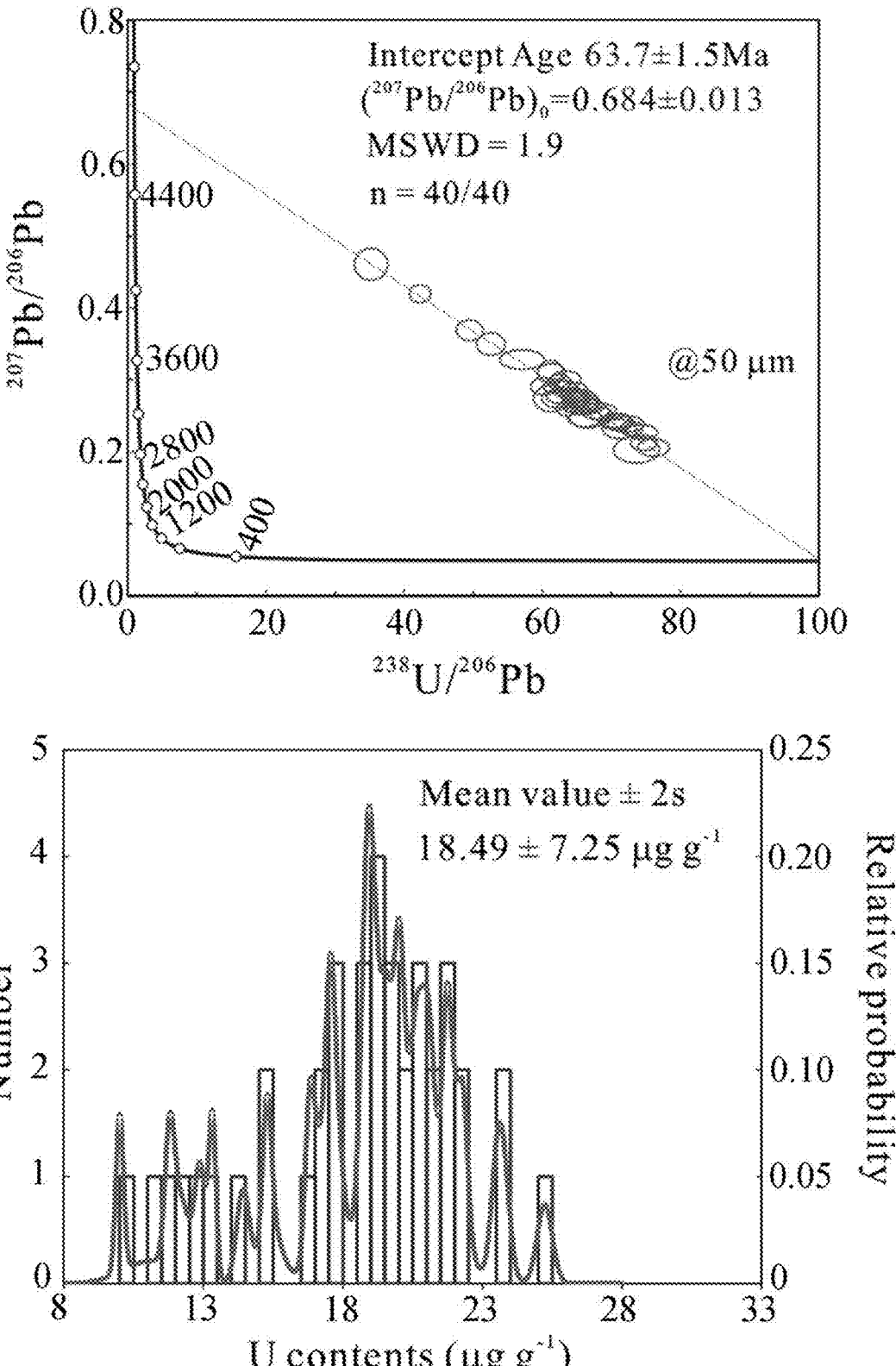
Figure 8A:
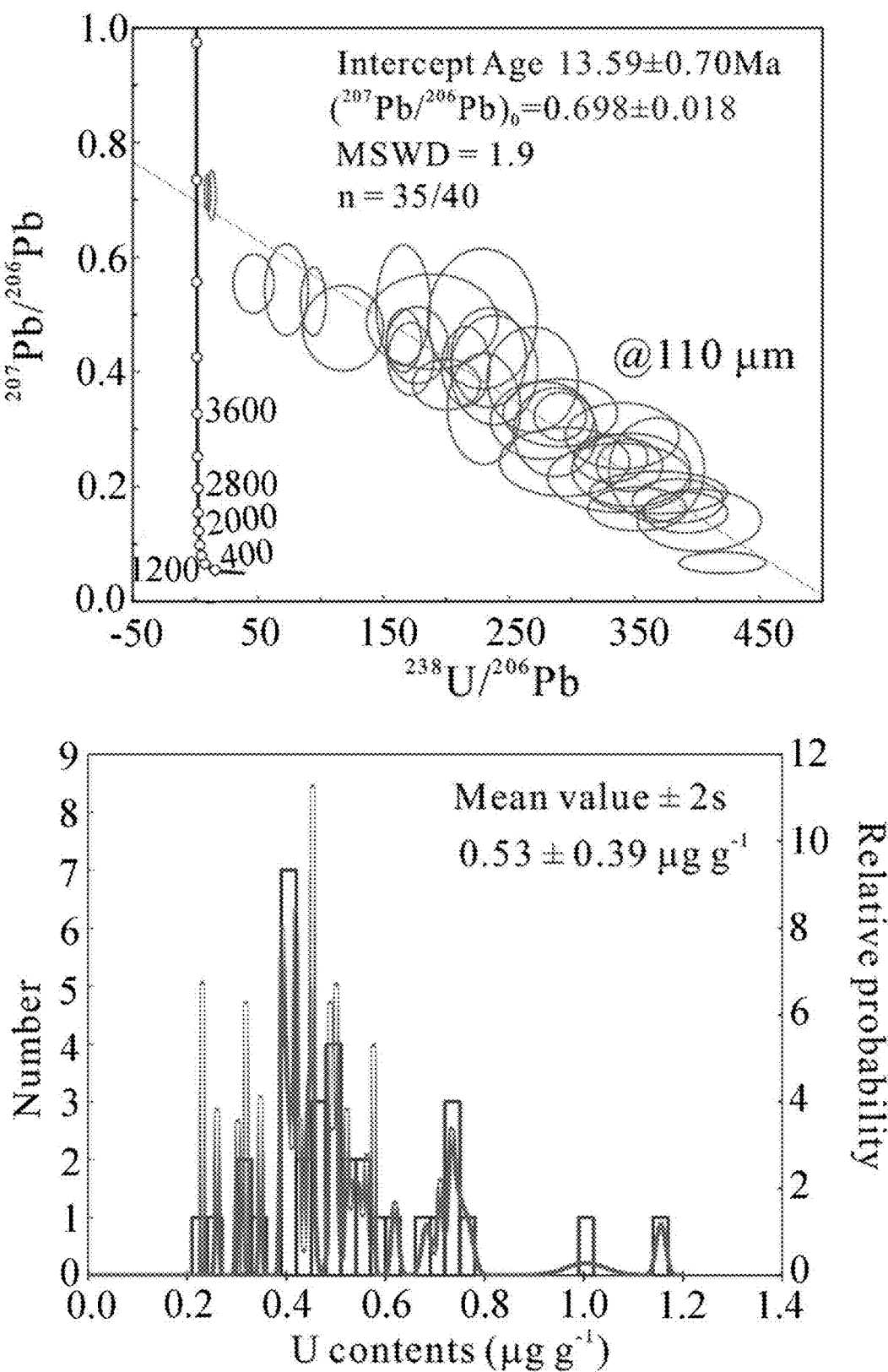
FIG. 8A-B show analysis result diagrams of JT in the example of the present disclosure, where
Figure 8B:
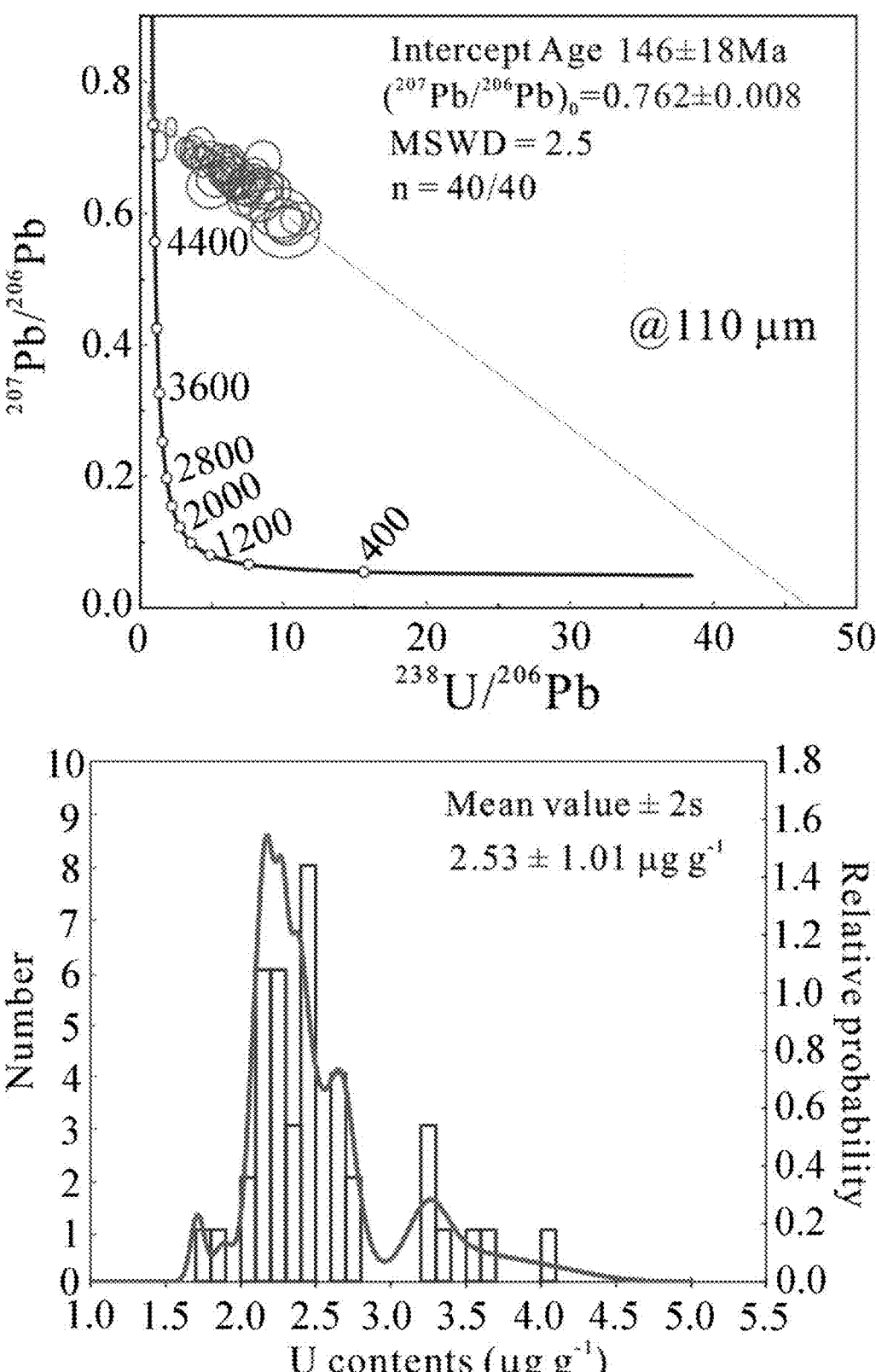
Figure 9A:
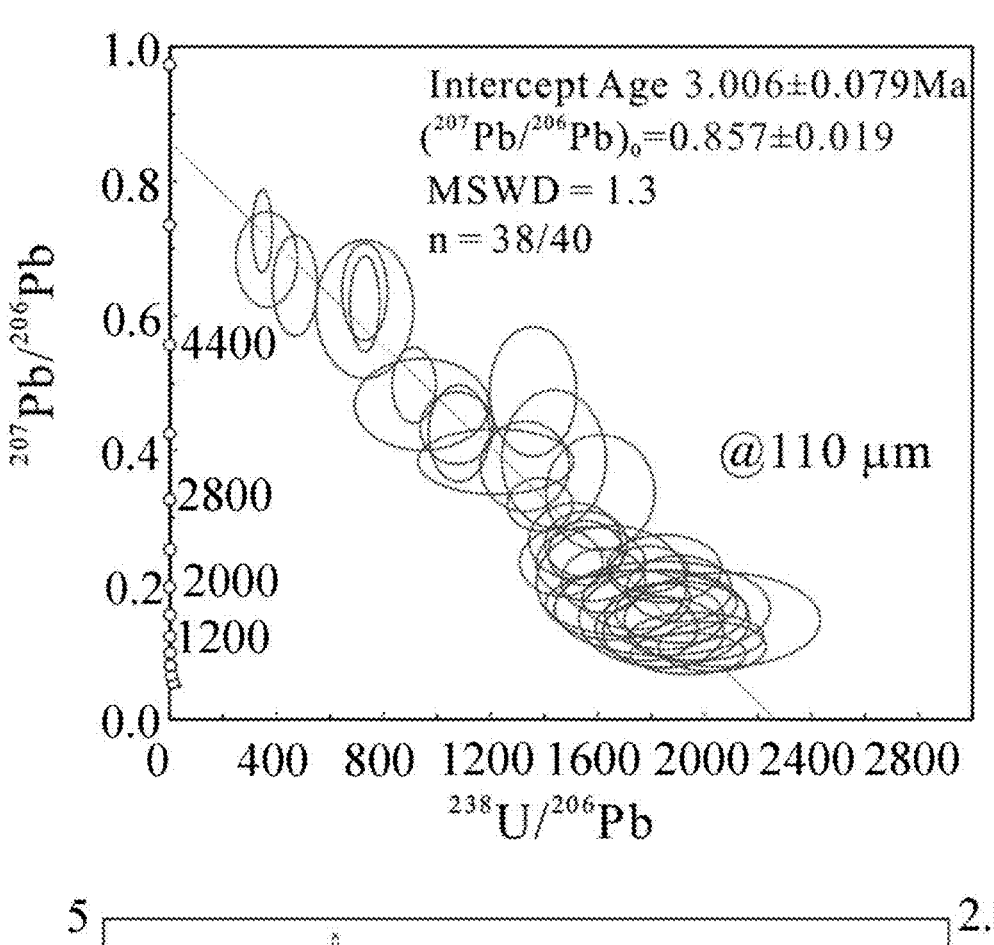
FIG. 9A-B show analysis results of ASH-15 in the example of the present disclosure, where FIG. 9A and FIG. 9B respectively represent results of two independent tests at different times, U contents of the two tests are also listed correspondingly, and a 110-micron laser beam spot is used.
Figure 9A:
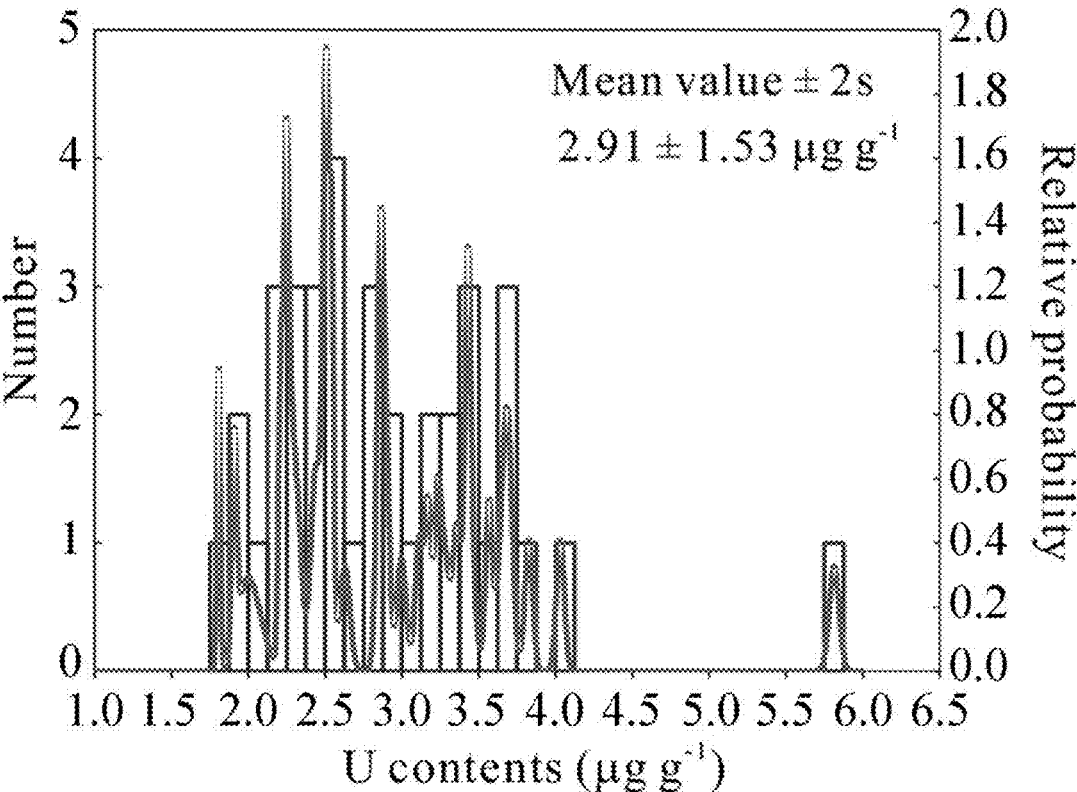
Figure 9B:
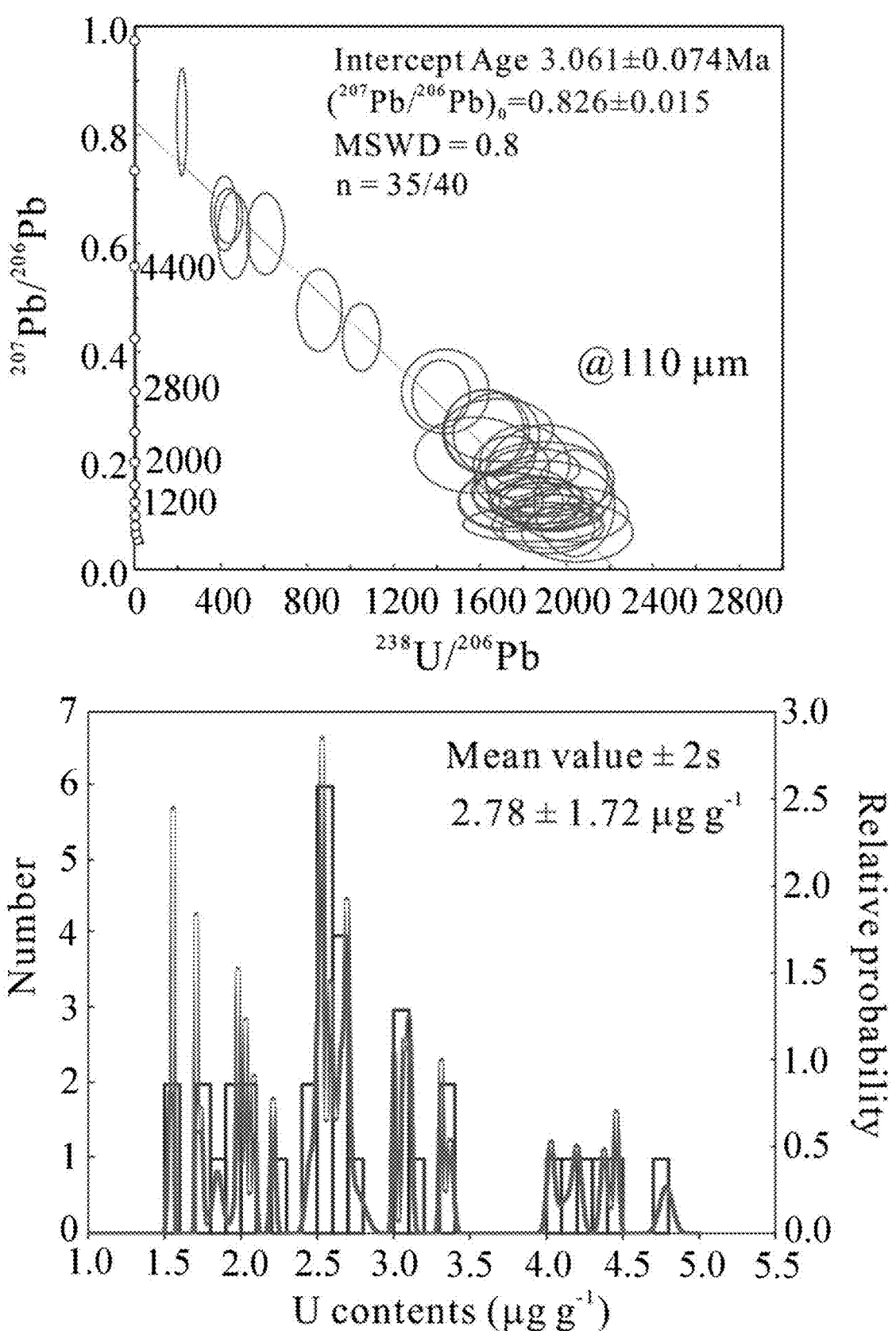

In order to further verify the influence of different instrument sensitivity modes on the experimental results, the present disclosure took JT calcite as the research object, and conducted U—Pb dating experiments under three modes. The experimental results are shown in FIG. 5A-C below. It can be seen from the figure that JT has the optimal result under the Jet+X cone group+nitrogen addition mode. In addition, the figure shows that only this mode can give accurate age data. To sum up, the experiments showed that the instrument had the optimal performance under the Jet+X-cone group+Ar-N₂ plasma mode, and could accurately determine the U—Pb age of calcite. With the optimized instrument sensitivity, JT could be dated with only 110 μm, which was significantly superior to the 150-200 μm previously reported.

In order to further verify the advantages of the two-step dating method for calcite provided by the present disclosure, namely (1) 2D element imaging, and (2) selection of an area with a high U content for U—Pb dating, the results of the two-step method and the one-step method are compared, as shown in FIG. 6. It can be seen from the figure that the success rate of the two-step method is obviously superior to that of the one-step method.

In order to further verify the reliability of the method, three calcite samples are analyzed, as shown in FIG. 7A-D, FIG. 8A-B, and FIG. 9A-B. It can be seen from the figure that the age results of the three calcite reference materials are consistent with the recommended values within the error range. The analysis accuracy is 2-3%.

In combination with the above data, the present disclosure provides an in situ U—Pb dating method for calcite, which can provide more favorable technical support for the application of calcite geochronology.

The data in the above examples were all completed on LA-ICP-MS of Photo Machine Analyst G2 excimer laser series thermoelectric Element XR ICP-MS. The cited examples were only used to explain the present disclosure, and not to limit the present disclosure. Those skilled in the art can obtain the same results on similar LA-ICP-MS instruments according to the method.

It will be appreciated by those of ordinary skill in the art that the examples herein are used for helping a reader to understand the implementation method of the present disclosure, and it should be understood that the protection scope of the present disclosure is not limited to such special statement and examples. Those of ordinary skill in the art may make other various specific modifications and combinations according to the technical teachings disclosed in the present disclosure without departing from the essence of the present disclosure, and such modifications and combinations still fall within the protection scope of the present disclosure.

What is claimed is:

1. An in situ U—Pb dating method for calcite, comprising the following steps:

a) cutting a calcite sample or a rock sample containing calcite to prepare an epoxy resin sample target with a diameter of 1 inch and a thickness of 5 mm to adapt to a size of a laser ablation sample chamber;

b) placing the sample in the laser ablation sample chamber, and adjusting a position of the sample in an optical axis direction to make a laser beam focus well;

c) conducting line scanning ablation on calcite in the sample target using the laser beam, loading ablated aerosol into a quadrupole inductively coupled plasma mass spectrometry (ICP-MS) plasma source for ionization using a helium gas as a carrier gas, and measuring ion signal intensity data of $^{43}Ca$, $^{88}Sr$, $^{139}La$, and $^{238}U$;

d) conducting two-dimensional (2D) element imaging using Iolite 4 software, processing data offline, conducting instrument blank deduction for a signal, and conducting instrument drift correction to calculate signal intensities of different elements; and calculating an instrument response coefficient according to a signal intensity and content of each element of NIST SRM 612, calculating a content of an unknown sample according to the instrument response coefficient, and imaging a 2D element content distribution map;

e) according to the 2D element content distribution map, determining a high-U analysis target area, conducting point ablation on the high-U target area using the laser beam, loading ablated aerosol into a double-focusing sector field ICP-MS plasma source for ionization using a carrier gas, and measuring ion signal intensity data of $^{206}Pb$, $^{207}Pb$, and $^{238}U$;

f) in a measurement process, after every ten unknown samples are tested, repeatedly testing two calibration reference materials NIST SRM 614 for $^{207}Pb/^{206}Pb$ correction, three calibration reference materials WC-1 for $^{238}U/^{206}Pb$ correction, and two quality monitoring reference materials Duff Brown Tank to ensure same measurement conditions for the reference materials and the unknown samples;

g) after the element signal data is obtained, obtaining corresponding fractionation coefficients according to measured values and standard values of $^{207}Pb/^{206}Pb$ and $^{238}U/^{206}Pb$ of the reference materials, and correcting $^{207}Pb/^{206}Pb$ and $^{238}U/^{206}Pb$ ratios of the unknown sample; and h) constructing a Tera-Wasserbug diagram through the corrected $^{207}Pb/^{206}Pb$ and $^{238}U/^{206}Pb$ ratios, and calculating age data and an initial Pb isotope ($^{207}Pb/^{206}Pb$) composition of the calcite sample.

\* \* \* \* \*